US010197556B2

(12) United States Patent
Smeets et al.

(10) Patent No.: US 10,197,556 B2
(45) Date of Patent: Feb. 5, 2019

(54) METHODS TO DETECT NON-GENOTOXIC CARCINOGENS USING FLATWORMS

(71) Applicants: Universiteit Gent, Ghent (BE); Universiteit Hasselt, Hasselt (BE)

(72) Inventors: Karen Smeets, Bilzen (BE); An-Sofie Stevens, Maaseik (BE); Michelle Plusquin, Bilzen (BE); Tom Artois, Diepenbeek (BE); Maxime Willems, Balegem (BE); Jean Paul Remon, Melle (BE)

(73) Assignees: Universiteit Gent, Ghent (BE); Universiteit Hasselt, Hasselt (BE)

( * ) Notice: Subject to any disclaimer, the term of this patent is extended or adjusted under 35 U.S.C. 154(b) by 0 days.

(21) Appl. No.: 15/557,930

(22) PCT Filed: Mar. 15, 2016

(86) PCT No.: PCT/EP2016/055524
§ 371 (c)(1),
(2) Date: Sep. 13, 2017

(87) PCT Pub. No.: WO2016/146620
PCT Pub. Date: Sep. 22, 2016

(65) Prior Publication Data
US 2018/0059095 A1    Mar. 1, 2018

(30) Foreign Application Priority Data
Mar. 16, 2015    (EP) .................................... 15159158

(51) Int. Cl.
*G01N 31/00* (2006.01)
*G01N 33/53* (2006.01)
*G01N 33/50* (2006.01)

(52) U.S. Cl.
CPC ..... *G01N 33/5017* (2013.01); *G01N 33/5085* (2013.01); *G01N 2333/43526* (2013.01); *G01N 2333/43539* (2013.01); *G01N 2333/47* (2013.01); *G01N 2440/14* (2013.01)

(58) Field of Classification Search
None
See application file for complete search history.

(56) References Cited

FOREIGN PATENT DOCUMENTS

WO    2016146620 A1    9/2016

OTHER PUBLICATIONS

Kokel et al., Abstract, The nongenotoxic carcinogens naphthalene and para-dichlorobenzene suppress apoptosis in Caenorhabditis elegans, Nature Chemical Biology, May 14, 2006, pp. 338-345, vol. 2, No. 6.
Plusquin et al., Physiological and molecular characterization of cadmium stress in Schmidtea mediterranea, The International Journal of Developmental Biology, pp. 183-191, Jan. 1, 2012, vol. 56, No. 1-2-3.
Stalmans et al., Flatworm models in pharmacological research: The importance of compound stability testing, Regulatory Toxicology and Pharmacology, Oct. 1, 2014, pp. 149-154, vol. 70, No. 1.
PCT International Search Report, PCT/EP2016/055524, dated May 6, 2016.
PCT International Written Opinion, PCT/EP2016/055524, dated May 6, 2016.
Validation and valorization of flatworms as model system in primary toxicity screenings, Dec. 31, 2014, Retrieved from the Internet on Sep. 7, 2017: http://www.uhasselt.be/UH/Research-groups/en-projecten_DOC/en-project_details.html?pid=5379&t=en; available at least as early as Dec. 31, 2014.
Best et al., Planarians as a Model System for In Vitro Teratogenesis Studies, Teratogenesis, Carciogenesis, and Mutagenesis, 1982, pp. 277-291, vol. 2.
Hall et al., Neoplastic Transformation in the Planarian: I. Cocarcinogenesis and Histopathology, The Journal of Experimental Zoology, 1986, pp. 211-227, vol. 240.
Schaeffer, David, Planarians as a Model System for in Vivo Tumorigenesis Studies, Ecotoxicology and Environmental Safety, 1993, pp. 1-18, vol. 25.
Stevens et al., Toxicity profiles and solvent-toxicant interference in the planarian Schmidtea Mediterranea after dimethylsulfoxide (DMSO) exposure, Journal of Applied Toxicology, 2014, pp. 319-326, vol. 35.
Stevens et al., Stem cell proliferation patterns as an alternative for in vivo prediction and discrimination of carcinogenic compounds, Scientific Reports, published May 3, 2017, 11 pages, DOI: 10.1038/srep45616.
Newmark et al., Bromodeoxyuridine Specifically Labels the Regenerative Stem Cells of Planarians, Developmental Biology, 2000, pp. 142-153, vol. 220.
Ladurner et al., Spatial Distribution and Differentiation Potential of Stem Cells in Hatchlings and Adults in the Marine *Platyhelminth macrostomum* sp.: A Bromodeoxyuridine Analysis, Developmental Biology, 2000, pp. 231-241, vol. 226.

*Primary Examiner* — Lisa V Cook
(74) *Attorney, Agent, or Firm* — TraskBritt, P.C.

(57) ABSTRACT

This disclosure relates to predicting the carcinogenicity of compounds. More in particular, this application discloses methods to detect whether a compound is a non-genotoxic carcinogen and methods to discriminate between genotoxic and non-genotoxic carcinogens based on in vivo stem cell proliferation patterns in flatworms.

7 Claims, 6 Drawing Sheets

METHODS TO DETECT NON-GENOTOXIC CARCINOGENS USING FLATWORMS

CROSS-REFERENCE TO RELATED APPLICATIONS

This application is a national phase entry under 35 U.S.C. § 371 of International Patent Application PCT/EP2016/055524, filed Mar. 15, 2016, designating the United States of America and published in English as International Patent Publication WO 2016/146620 A1 on Sep. 22, 2016, which claims the benefit under Article 8 of the Patent Cooperation Treaty to European Patent Application Serial No. 15159158.3, filed Mar. 16, 2015.

TECHNICAL FIELD

This application relates to predicting the carcinogenicity of compounds. More in particular, this application discloses methods to detect or predict whether a compound is a non-genotoxic carcinogen and methods to discriminate between genotoxic and non-genotoxic carcinogens based on in vivo stem cell proliferation patterns in flatworms.

BACKGROUND

A correct assessment of cancer risks associated with human exposure to chemicals is of great importance from both public health and economic perspectives. In this regard, accurate and reliable tests that estimate the carcinogenic potency of compounds are indispensable. The two-year rodent carcinogenicity bioassay is the gold standard for carcinogenic screenings of newly developed drugs and other chemical compounds, but high costs, long experimental periods and European (REACH) and U.S. (ICCVAM Authorization Act) policies promote the search for alternative assays (1-5). In addition, because of raising ethical concerns regarding animal use in scientific procedures, organizations like EURL ECVAM (European Union Reference Laboratory for the Validation of Alternative Methods) and ICCVAM (Interagency Coordinating Committee on the Validation of Alternative Methods) have been founded to validate alternative approaches in accordance with the 3Rs (Replace, Reduce and Refine) Declaration, which includes the use of organisms with limited sentience such as invertebrates.

A challenge for the development of alternative test methods is that, besides an adequate estimation of carcinogenicity, compounds need to be classified according to their presumed predominant mechanism of action into genotoxic and non-genotoxic carcinogens, which entail different assessments of human cancer risk. Genotoxic carcinogens disturb the genomic integrity directly by interacting with the DNA and/or the cellular apparatus, and are assumed to have a low-dose linearity without dose thresholds in their carcinogenic effects. Non-genotoxic carcinogens alter gene expression indirectly and promote tumor growth by interfering with a variety of cellular processes associated with suppressed apoptosis and increased cell proliferation (6-8). A major difficulty in distinguishing these classes of carcinogens is the comparison of exposure conditions, since multiple signaling pathways are deregulated during non-genotoxic carcinogenesis, whereby carcinogenic effects only occur if a certain threshold dose is reached (7-10). The understanding and prediction of non-genotoxic carcinogens is substantially complicated by their compound-specific mechanisms of action (7, 10).

The present alternative, in vitro and short term in vivo assays, identify the majority of genotoxic carcinogens, although improvements in the predictive capacity are still needed to diminish false positive and negative results. Standard in vitro assays for the detection of genotoxic compounds produce up to 70% and more of irrelevant positive results, which require expensive and time-consuming follow-up in vitro and in vivo testing. Another drawback of these tests is the sensitivity and reliability in detecting non-genotoxic carcinogens, which represent up to 25% of Class I human carcinogens according to the International Agency for Research on Cancer (IARC) (3, 5, 7, 11-13). A better understanding of cellular and molecular events involved in non-genotoxic carcinogenesis is needed and, given the extensiveness and complexity of these processes, in vitro detection methods may not be sophisticated enough to cover the full carcinogenicity response.

Flatworms are promising organisms for predictive carcinogenicity/genotoxicity screenings for the following reasons: (1) Their remarkable regeneration capacity, rebuilding missing body parts within about one week, enables the study of carcinogen-induced responses during the regeneration of multiple tissues (14, 15). Since massive cell proliferation is a prerequisite for both regeneration and carcinogenesis, the organism's cellular response to carcinogen exposures is accelerated during the process of regeneration (16-18). (2) Their experimentally accessible stem cells enable in vivo studies of carcinogen-induced responses of pluripotent, adult stem cells within the entire animal. (3) The main characteristics of chemically induced carcinogenesis, namely, the initiation and promotion stage of neoplastic formation, are described in flatworms and several underlying cancer-related genes and signaling pathways have been identified, e.g., PTEN, FOXO, caspases, cyclins, (PI3K)-Akt pathway, RAS pathway, p53 pathway, and MAPK pathway (19-24).

Stalmans et al. (25) further disclose an in vivo flatworm carcinogenicity bioassay, in which stem cell proliferation is used as an endpoint to assess the carcinogenic potential of compounds. However, it is completely unknown whether flatworms can be used to detect whether a compound is a non-genotoxic carcinogen and/or whether flatworms can be used to distinguish non-genotoxic carcinogens from genotoxic carcinogens.

BRIEF SUMMARY

This application discloses methods of predicting or detecting whether a compound is a non-genotoxic carcinogen and methods of discriminating between genotoxic and non-genotoxic carcinogens based on in vivo stem cell proliferation patterns in flatworms. Hence, it is clear that the methods of this disclosure can also be used to predict or detect whether a compound is a genotoxic carcinogen.

A first embodiment of the disclosure relates to an in vivo method of predicting whether a compound is a non-genotoxic carcinogen comprising:
  exposing the compound to flatworms for a period of time,
  counting the number of adult pluripotent stem cells within the flatworms after exposure to the compound, and
  comparing the latter number to a reference cut-off value,
  wherein the compound is a non-genotoxic carcinogen when the number of adult pluripotent stem cells is greater than the cut-off value.

The term "compound" means any compound that might be carcinogenic. Non-limiting examples are the genotoxic carcinogens methyl methane sulfonate (MMS; Cas # 66-27-

3; purity 99%), cyclophosphamide monohydrate (CP, Cas # 6055-19-2) and 4-Nitroquinoline-1-oxide (4NQO, Cas # 56-57-5), the non-genotoxic carcinogens diethylstilbestrol (DES, Cas # 56-53-1), methapyrilene hydrochloride (MPH; 135-23-9; analytical standard), cyclosporine A (CsA; Cas # 59865-13-3; purity ≥98.5%), chlorpromazine (CPZ; Cas # 69-09-0; purity ≥98%) and sodium phenobarbital (S-PB; Cas # 57-30-7) and the non-carcinogens d-mannitol (Dmann, Cas # 69-65-8) and sulfisoxazole (Sox, Cas # 127-69-5). The "compounds" can be selected on the basis of available in vitro and in vivo data reported in the OECD DRP31 document (26), IARC classifications and the publications by Kirkland et al. (13, 27) and Robinson and MacDonald (28). Based on these publications, a distinction can be made between genotoxic carcinogens, non-genotoxic carcinogens and non-carcinogens. A "carcinogen" is defined as any chemical of which the carcinogenic potential has been clearly demonstrated in a two-year rodent bioassay. A "genotoxic carcinogen" must have shown to be positive in classical in vitro and in vivo genotoxicity assays. CP and 4NQO are non-limiting examples of non-genotoxic (i.e., requiring metabolization) and genotoxic carcinogens, respectively. A "non-genotoxic carcinogen" is any chemical of which a non-DNA-reactive mechanism is the primary cause for the observed carcinogenic effects in mammalians and humans. DES and CA are non-limiting examples of non-genotoxic carcinogens. A compound that is negative in the standard in vitro and in vivo genotoxicity tests and that lacks carcinogenic potential in the two-year mouse and rat bioassays is considered "non-carcinogenic." Dmann and Sox are non-limiting examples of non-carcinogens.

The terms "exposing the compounds to flatworms" mean any method known to a skilled person that allows contact between the compound to be tested and the flatworms. A non-limiting example of a procedure of "exposing the compounds to flatworms" is the following:

One week before starting chemical exposure, a six-well plate filled with 4 ml f/2 medium (Novolab NV) is inoculated with diatoms to achieve an ad libitum food source during exposure. Starvation of the worms leads to a decrease in stem cell proliferation (as shown in Nimeth et al. (29)), which would interfere with stem cell proliferation, the endpoint of the assay. Before the start of exposure, fifteen adult worms per condition are pipetted in each well, which is then emptied by pipetting without drying out the worms and refilled with f/2 medium (control), if required F2+0.05% DMSO (vehicle control) and a selected concentration of the chemical.

The DMSO concentration in the vehicle control should never exceed 0.05% in order to be able to reliably observe any behavioral or toxic effects of compounds in these animals (30-32).

To select the appropriate compound concentration, first, a broad concentration range-finding experiment (spacing factor 10; two weeks exposure) can be carried out. Based on this pilot range finding, a fine-tuned range finding (spacing factor less than or equal to 2; for D-Mannitol factor 5) can be chosen to conduct the assay. The maximum concentration tested depends on the test compound solubility and the requirement of a survival of twelve out of fifteen worms at the end of exposure.

The medium can be refreshed weekly.

The term "flatworm" means relatively simple bilaterian, unsegmented, soft-bodied invertebrates belonging to the phylum Platyhelminthes. Non-limiting examples are the flatworm species *Macrostomum lignano* and *Schmidtea mediterranea*.

The term "a period of time" with regard to this first embodiment means different exposure times ranging from one day to six weeks and specifically relates to a time period of about two weeks (i.e., 10, 11, 12, 13, 14, 15, 16, 17 or 18 days).

Hence, and more specifically, this disclosure also relates to an in vivo method as indicated above wherein the period of time is two weeks.

The terms "adult pluripotent stem cells (APSC)" mean undifferentiated cells in an adult organism that divide to give rise to another stem cell and can differentiate to any cell type.

The terms "a reference cut-off value" with regard to this first embodiment means a specific value that is used as a reference value in order to conclusively decide whether a compound to be tested is a non-genotoxic or genotoxic carcinogen or in order to conclusively decide whether a compound to be tested is a non-carcinogen. The cut-off value can be determined based on density plots (R version 2.15.3; (33)) of the number of mitotic stem cells of all experiments for controls (such as sea water and DMSO), non-carcinogens, genotoxic carcinogens and non-genotoxic carcinogens.

The terms "greater than the cut-off value" with regard to this first embodiment means that the number of mitotic stem cells exceeds the cut-off value.

A compound can be considered positive if the following criteria are met: 1) a minimum of 20% of the worms per concentration must have a number of mitotic stem cells greater than or equal to the cut-off value of 30. Thirty (30) can lay in the tail of the distribution corresponding to the 97.5 percentile or 2 standard deviations. Concentrations resulting in the death of 20% of the worms (three out of fifteen) during exposure can be considered cytotoxic and should not be analyzed. The following criteria can be set for a successful test: 1) minimum three independent experiments, 2) the number of mitotic stem cells of two subsequent chemical concentrations should be provided, 3) the number of mitotic stem cells of minimum five worms per concentration should be quantified and, finally, 4) a maximum of two individual control worms (e.g., seawater and DMSO) with a number of mitotic stem cells greater than or equal to the cut-off value of 30.

Hence, a compound can be considered positive if the following criteria are met: 1) a minimum of 20% of the worms per concentration should have a number of mitotic stem cells greater than or equal to the cut-off value of 30 (scored as "+") and 2) at least two-thirds of the experiments should have received a "+" score for the compound to have an overall final "+" call. In the future, two experiments would be sufficient to determine the overall call, a third experiment would only be required when the number of "+" and "−" are equal. Plots can be generated using the software package R as described above.

Hence, it is clear that the methods as described in detail in the Examples, or any other method to count the number of stem cells or to assess stem cell proliferation patterns such as (fluorescent) in situ hybridization, immunolabelling, bromodeoxyuridine staining, transgenic lines, etc., can be used to predict or detect whether a compound is a genotoxic carcinogen. The latter methods to count the number of stem cells or to assess stem cell proliferation patterns are, for example, described in: 1) K. Nimeth et al., "Regeneration in *Macrostomum lignano* (Platyhelminthes): cellular dynamics in the neoblast stem cell system," *Cell Tissue Res.* (2007) 327:637-646; 2) B. Pearson et al., "A Formaldehyde-based Whole-Mount In Situ Hybridization Method for Planarians,"

*Dev. Dyn.* (2009) 238(2):443-450; and 3) R. King and P. Newmark, "In situ hybridization protocol for enhanced detection of gene expression in the planarian *Schmidtea mediterranea,*" *BMC Developmental Biology* (2013) 13:8.

A second embodiment of the disclosure relates to an in vivo method of detecting whether a compound is a non-genotoxic carcinogen and/or distinguishing a non-genotoxic carcinogen from a genotoxic carcinogen comprising:

exposing the compound or the non-genotoxic carcinogen and genotoxic carcinogen for a period of time at concentrations that trigger phenotypic effects to regenerating flatworms, counting the number of adult pluripotent stem cells within the regenerating flatworms after exposure, and comparing the latter number to the number obtained by a similar exposure to a non-carcinogenic, control compound, wherein a compound is a non-genotoxic carcinogenic compound when the number of adult stem cells at the time of appearance of systemic effects is similar to the number of adult stem cells when the control, non-carcinogenic compound is used, and wherein a compound is a genotoxic carcinogenic compound when the number of adult stem cells at the time of appearance of systemic effects is significantly lower than the number of adult stem cells when the control, non-carcinogenic compound is used.

The terms "exposing the compound or the non-genotoxic carcinogen and genotoxic carcinogen for a period of time at concentrations that trigger phenotypic effects to regenerating flatworms" mean, first, that the described methods are performed with regenerating animals (heads and tails) in order to elicit accelerated initial responses to carcinogenic compounds as this process of massive cell proliferation, migration and differentiation resembles best the process of carcinogenesis (16, 32). The terms further indicate that food must be withheld from the flatworms for one week prior to measurements. In each experimental condition, for example, four regenerating animals cut transversally immediately before exposure, can be placed in six-well plates containing, for example, 4 ml of a carcinogen/compound concentration, medium (control) or medium with 0.05% DMSO (vehicle control). To exclude intrinsic effects of DMSO on cell proliferation, the DMSO vehicle concentration should never exceed 0.05% and interaction effects between the test compound and DMSO can be investigated using a two-way ANOVA (32). After comparing continuous versus intermittent exposures and medium refreshment once versus twice a week, a continuous exposure with medium refreshment twice a week may be found most suitable to obtain distinctive cellular responses.

The term "regenerating flatworm" means that flatworms have the capacity to replace large regions of missing structures through regeneration. When an animal is artificially cut, the regeneration process is initiated (start regeneration) and ends (depending on the size of the missing piece) after about one to two weeks depending on the site of amputation (34).

The terms "a similar exposure to a non-carcinogenic, control compound" means that the experimental set-up of exposure was the same as the treatment scheme for the carcinogenic compound. It should be clear that an alternative to "comparing to a similar exposure to a non-carcinogenic, control compound" can be "comparing to the number of adult pluripotent stem cells of a non-exposed, control flatworm or comparing to the number of adult pluripotent stem cells of a control flatworm exposed to medium wherein there is no addition of a control compound (sham-exposed)."

The phenotypic effects that can be monitored daily after exposure during a certain period of time (i.e., after three days, to about 14 days) are tissue regression (=areas of the worm's body in which tissue is missing without the appearance of wounds), lesions (=areas of the worm's body in which tissue is missing and wounds appear), blisters (=small pockets of fluid within the worm's skin layer), bloating (=abnormal swelling of the worm's body), pigmentation (=areas with a visual increase in pigmentation), behavioral changes such as jerky movements or curling around their ventral surface, difficulties in regeneration, abnormal body size, tissue outgrowth, flattened posture and death (35).

Therefore, and more in particular, this disclosure relates to an in vivo method as described above wherein the phenotypic effects are aberrant pigmentation spots, tissue regression, lesions, blisters, bloating, behavioral changes, difficulties in regeneration, abnormal body size, tissue outgrowth and flattened posture.

The time period after which the phenotypic effects are usually detected and that allows distinguishing between genotoxic and non-genotoxic compounds is variable and can be about three days (i.e., 2, 3, 4 or 5 days post-exposure) or can be about a week (i.e., 6, 7, or 8 days post-exposure) or can be about two weeks (i.e., 9, 10, 11, 12, 13, 14, 15, 16, 17, 18, or 19 days post-exposure). Therefore, and more in particular, this disclosure relates to an in vivo method as described above wherein the time period that triggers phenotypic effects to regenerating flatworms is between 3 and 19 days.

The terms "concentrations that trigger phenotypic effects" mean chemical concentrations of the selected compounds as indicated above with regard to a first embodiment (such as, for example, MMS: 500 $\mu$M; 4NQO: 2 $\mu$M; S-PB: 2 mM; CPZ: 1 $\mu$M; MPH: 150 $\mu$M) where phenotypic (morphological, behavioral) effects as indicated above could be observed.

The terms "similar or lower than the number of adult stem cells when the control, non-carcinogenic compound is used" mean:

a) "Similar" means that the average number of cells (value 1) of controls/non-carcinogen do not differ from the observed non-genotoxic compound specific (value 2) ($p > 0.05$);

b) "Lower" means that the average number of cells after exposure to a specific genotoxic compound is significantly lower ($p < 0.05$) than, e.g., a control value. P-values less than 0.05 are considered statistically significant.

A third embodiment of the disclosure relates to an in vivo method of predicting whether a compound is a non-genotoxic carcinogen and/or distinguishing a non-genotoxic carcinogen from a genotoxic carcinogen comprising:

exposing the compound or the non-genotoxic carcinogen and genotoxic carcinogen for at least three days to regenerating flatworms, counting the number of adult pluripotent stem cells within the regenerating flatworms after the exposure, and comparing the latter number to the number obtained by a similar exposure to a non-carcinogenic, control compound, wherein a compound is a non-genotoxic carcinogenic when there is a concentration-dependent increase in the number of adult pluripotent stem cells at day 3 post-exposure, wherein a compound is a genotoxic carcinogenic when there is a concentration-dependent decrease in the number of adult pluripotent stem cells at day 3 post-exposure, and, wherein, a compound is non-carcinogenic when there is no concentration-dependent response in the number of adult pluripotent stem cells at day 3 post-exposure.

A comparison of proliferative responses of adult planarian stem cells during the initial stages of regeneration, namely after one and three days of exposure, discriminates genotoxic carcinogens from non-genotoxic and non-carcinogens. Genotoxic carcinogens are characterized by significantly fewer mitotic cells after three days of exposure in comparison with a one-day exposure set-up, while non-genotoxic carcinogens are characterized by significantly more mitotic cells after three days of exposure in comparison with a one-day exposure set-up. Non-carcinogenic compounds show no differences between one and three days of exposure, clearly discriminating them from non-genotoxic and genotoxic carcinogens.

The terms "a concentration-dependent increase or decrease" describes the relationship between the chemical concentration of the compound and the average number of stem cells. Higher concentrations result in an increase in the number of stem cells for a carcinogenic class (non-genotoxic carcinogens) and a decrease in the other class (genotoxic carcinogens), respectively.

The term "for at least three days" with regard to the third embodiment means that the exposure time to the carcinogens should last 3, 4, 5, . . . days in order to be able to make a comparison with a one-day exposure set-up as is described above.

The terms "a similar exposure to a non-carcinogenic, control compound" means that the experimental set-up of exposure was the same as the treatment scheme for the carcinogenic compound.

It should be clear that an alternative to "comparing to a similar exposure to a non-carcinogenic, control compound" can be "comparing to the number of adult pluripotent stem cells of a non-exposed, control flatworm or comparing to the number of adult pluripotent stem cells of a control flatworm exposed to medium wherein there is no addition of a control compound (sham-exposed)."

More in particular, this disclosure relates to an in vivo method as described above concerning all three embodiments wherein the flatworm is *Macrostomum lignano* or *Schmidtea mediterranea*. The latter species are described by Ladurner et al. (36, 37) and Benazzi et al. (38), respectively.

More in particular, this disclosure relates to an in vivo method as described above wherein the number of stem cells is quantified by a phosphorylated histone H3 immunoassay. The latter assay is in detail described by Ladurner et al. (36) and Newmark and Alvarado (39).

Hence, this disclosure relates to the usage of flatworms to detect whether a compound is a non-genotoxic carcinogen and/or to distinguish a non-genotoxic carcinogen from a genotoxic carcinogen.

More in particular, this disclosure relates to the usage as described above, wherein the flatworm is *Macrostomum lignano* or *Schmidtea mediterranea* as defined above.

BRIEF DESCRIPTION OF THE DRAWINGS

FIG. 4: Time profile of stem cell proliferation responses in response to carcinogen exposures. Mitotic divisions per $mm^2$ after one day, three days, one week and two weeks exposure to a genotoxic (MMS), non-genotoxic (CsA) and non-carcinogen (Dmann). The mitotic divisions after six weeks exposure to MMS and CsA are also represented. The number of mitotic cells was normalized against the total body area of the worms and expressed relative to the corresponding MMS, CsA and Dmann control group per time point, respectively, culture medium, culture medium with 0.05% DMSO (vehicle control) and culture medium. Average cell proliferation values at each time point are connected by lines, individual measurements are also represented (≥3 per time point). Significant effects are indicated in the table: *$p<0.1$; $p<0.05$; *$p<0.01$. The average and se of MMS control groups are: 172.0±21.9 cells/$mm^2$ (1 day); 368.6±37.4 cells/$mm^2$ (3 days); 347.5±8.9 cells/$mm^2$ (1 week); 83.8±26.0 cells/$mm^2$ (2 weeks); 80.3±9.7 cells/$mm^2$ (6 weeks). The average and se of CsA control groups are: 344.1±42.5 cells/$mm^2$ (1 day); 328.3±46.6 cells/$mm^2$ (3 days); 288.8±17.7 cells/$mm^2$ (1 week); 180.9±15.8 cells/$mm^2$ (2 weeks); 74.9±11.6 cells/$mm^2$ (6 weeks). The average and se of Dmann control groups are: 352.5±42.2 cells/$mm^2$ (1 day); 317.7±26.9 cells/$mm^2$ (3 days); 260.6±44.0 cells/$mm^2$ (1 week); 135.9±15.6 cells/$mm^2$ (2 weeks). MMS=methyl methane sulphonate; CsA=cyclosporine A; and Dmann=d-mannitol.

352.5±42.2 cells/mm$^2$ (1 day); 317.7±26.9 cells/mm$^2$ (3 days). MMS=methyl methane sulphonate; 4NQO=4-nitroquinoline-1-oxide; CsA=cyclosporine A; S-PB=sodium phenobarbital; and Dmann=D-mannitol.

DETAILED DESCRIPTION

This disclosure will now be illustrated by the following non-limiting examples.

EXAMPLES

Example 1

In Vivo Methods to Detect Whether a Compound is a Non-genotoxic Carcinogen

Material and Methods
Chemicals and Compound Selection Strategy

Cyclophosphamide monohydrate (CP, Cas # 6055-19-2), Cyclosporin A (CA, Cas # 59865-13-3), Diethylstilbestrol (DES, Cas # 56-53-1), D-mannitol (Dmann, Cas # 69-65-8), 4-Nitroquinoline-1-oxide (4NQO, Cas # 56-57-5) and Sulfisoxazole (Sox, Cas # 127-69-5), were all purchased from Sigma Aldrich. These chemicals were selected on the basis of available in vitro and in vivo data reported in the OECD DRP31 document (26), IARC classifications and the publications by Kirkland et al. (13, 27) and Robinson and MacDonald (28). Based on these publications, a distinction was made between genotoxic carcinogens, non-genotoxic carcinogens and non-carcinogens. A carcinogen is defined as any chemical of which the carcinogenic potential has been clearly demonstrated in a two-year rodent bioassay. A genotoxic carcinogen must have shown to be positive in classical in vitro and in vivo genotoxicity assays. CP and 4NQO were selected as non-genotoxic (i.e., requiring metabolization) and genotoxic carcinogens, respectively. A non-genotoxic carcinogen is any chemical of which a non-DNA-reactive mechanism is the primary cause for the observed carcinogenic effects in mammalians and humans. DES and CA were selected as non-genotoxic carcinogens. A compound that is negative in the standard in vitro and in vivo genotoxicity tests and that lacks carcinogenic potential in the two-year mouse and rat bioassays is considered non-carcinogenic. Dmann and Sox were selected as non-carcinogens.

Animal Culture

Cultures of *Macrostomum lignano* (37) were grown in artificial seawater (ASW) enriched with f/2-medium (40) and fed ad libitum with the diatom *Nitzschia curvilineata* (PAE culture collection; UGent on the World Wide Web at pae.ugent.be/collection.htm), as described in references 41 and 43.

Test Procedure

One week before starting chemical exposure, a six-well plate filled with 4 ml f/2 medium (Novolab NV) was inoculated with diatoms to achieve an ad libitum food source during exposure. Starvation of the worms leads to a decrease in stem cell proliferation (as shown in Nimeth et al (29)), which would interfere with stem cell proliferation, the endpoint of the assay. Before the start of exposure, fifteen adult worms per condition were pipetted in each well, which was then emptied by pipetting without drying out the worms and refilled with f/2 medium (control), if required, F2+0.05% DMSO (vehicle control) and a concentration of the chemical.

The DMSO concentration in the vehicle control never exceeded 0.05%. This represented the maximum DMSO percentage in the chemical's highest test concentration. Literature data demonstrated that DMSO concentrations greater than 0.1% should be avoided in order to be able to reliably observe any behavioral or toxic effects of compounds in these animals (30-32).

To select the appropriate compound concentration, first, a broad concentration range-finding experiment (spacing factor 10; two weeks exposure) was carried out. Based on this pilot range finding, a fine-tuned range finding (spacing factor less than or equal to 2; for D-Mannitol factor 5) was chosen to conduct the assay. The maximum concentration tested depended on the test compound solubility and the requirement of a survival of twelve out of fifteen worms at the end of exposure.

For all chemicals investigated in this disclosure, the medium was refreshed weekly.

After a preliminary test (CP as reference) on different exposure times ranging from two days to six weeks, the worms were exposed for a period of two weeks, after which they were subjected to phosphorylated histone H3 immunostaining (PH3) to quantify mitosis.

PH3 Immunohistochemistry and Quantification

To quantify mitotic cells in whole mount specimens, the mitotic marker anti-PH3 was used. The staining was performed by first relaxing the animals in a 1:1 mixture of MgCl$_2$.6H$_2$O (7.14%) and ASW (5 minutes), then in MgCl$_2$.6H$_2$O (7.14%) (undiluted, 5 minutes), followed by fixation in paraformaldehyde (PFA, 4% in PBS, 60 minutes). Animals were then rinsed with phosphate-buffered saline (PBS, 3×5 minutes) and blocked in bovine serum albumin, containing TRITON® (BSA-T, 0.1% TRITON® X-100, 60 minutes). Subsequently, animals were incubated in primary rabbit-anti-phos-H3 (1:300 in BSA-T, overnight, 4° C., Upstate Biotechnology), rinsed in PBS (3×5 minutes) and incubated in secondary TRITC-conjugated swine-anti-rabbit (1:150 in BSA-T, 1 hour, DAKO). Finally, animals were washed with PBS (3×5 minutes) and slides were mounted using Vectashield (Vector Laboratories). Slides were analyzed using a Leica 2500P microscope equipped with epifluorescence, a 40× objective and a DFC360FX CCD camera.

Figure 1:
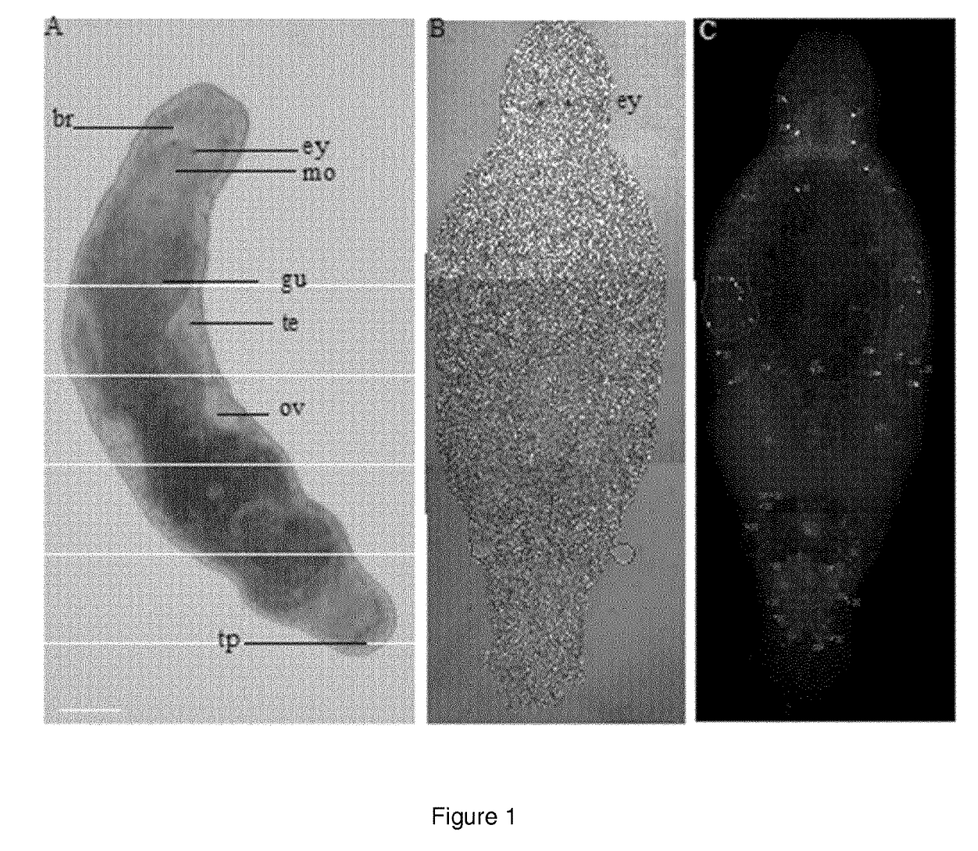
FIG. 1: Panel A, Interference contrast image of adult *Macrostomum lignano*; br: brain, ey: eyes, gu: gut; ov: ovary; te: testis tp: tail plate. Panels B and C, Interference contrast image and corresponding confocal projection of *M. lignano* labeled with an anti-phosphorylated histone H3 antibody. Cells in mitosis (white signal) are counted (marked X). Mitotic cells in the testes (outline pseudo-colored blue) are not part of the analysis. Anterior is to the top. Scale bar: 50 µm.

All somatic PH3-positive cells were counted manually using the Image J cell counter plugin (44) (FIG. 1). Gonadal PH3+ cells were not included in the analysis because of 1) the high density of divisions in that region that can lead to overlapping signals and 2) the germ line representing a separate population of cells, differentially tolerant to exposure, which can result in quantification variability.

Acceptance Criteria and Statistics

The cut-off value of the assay was determined based on density plots (R version 2.15.3; (33)) of the number of mitotic stem cells of all experiments for controls (sea water and DMSO), non-carcinogens, genotoxic carcinogens and non-genotoxic carcinogens. The cut-off value of 30 lays in the tail of the distribution corresponding to the 97.5 percentile or two standard deviations.

Concentrations resulting in the death of 20% of the worms (three out of fifteen) during exposure were considered cytotoxic and were not analyzed. The following criteria were set for a successful test: 1) minimum three independent experiments, 2) the number of mitotic stem cells of two subsequent chemical concentrations must be provided, 3) the number of mitotic stem cells of minimum five worms per concentration must be quantified and finally 4) to account for the possibility of negative control worms exhibiting mitotic numbers exceeding cut-off value, a maximum of two individual control worms (seawater and DMSO) with a number of mitotic stem cells greater than or equal to the cut-off value of 30 is tolerated.

Evaluation Criteria

A compound was considered positive if the following criteria were met: 1) a minimum of 20% of the worms per concentration must have a number of mitotic stem cells greater than or equal to the cut-off value of 30 (scored as "+") and 2) at least two out of three of the experiments must have received a "+" score for the compound to have an overall final "+" call. In the future, two experiments would be sufficient to determine the overall call, a third experiment would only be required when the number of "+" and "−" are equal. Plots were generated using the software package R.

Results

During the multistage process of chemical carcinogenesis, intracellular alterations can result in increased cellular proliferation. The endpoint of the in vivo flatworm stem cell proliferation assay is the number of mitotic stem cells. Carcinogens were expected to cause an increase in stem cell proliferation (+ result) and non-carcinogens to have no effect on proliferation after an exposure of two weeks (− result).

Figure 2:
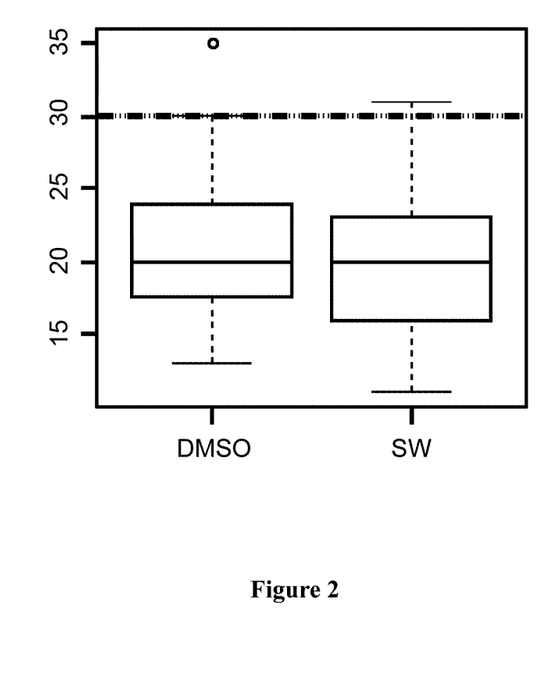
FIG. 2: Box plots representing the mean and IQR of the number of mitotic stem cells in seawater (SW; n=12) and solvent (DMSO; n=6) controls for all experiments used to determine the cut-off value for the validation criteria. The dashed line represents the cut-off value of the assay.

A control database was built on the number of mitotic cells per negative control animal. The cut-off value of the assay was determined by the analysis of the density plots of the number of mitotic stem cells for all controls in all experiments (FIG. 2).

All controls fulfilled the acceptance criteria of less than two worms per experiment exhibiting a number of mitotic stem cells greater than or equal to the cut-off value. For seawater controls (mean 20.1; n=232) the number of mitotic stem cells was maximally 38 and 50% of the counts were found between 17 and 28 cells. For DMSO controls (mean 21.0; n=89) the number of mitotic stem cells was maximally 35 and 50% of the counts were found between 18 and 24 cells. In all controls, the number of mitotic stem cells were less than 30 with a few exceptions (five out of 232 worms for seawater and four out of 89 in DMSO controls). As such, the cut-off value was set to 30 mitotic stem cells.

Non-carcinogens

Figure 3:
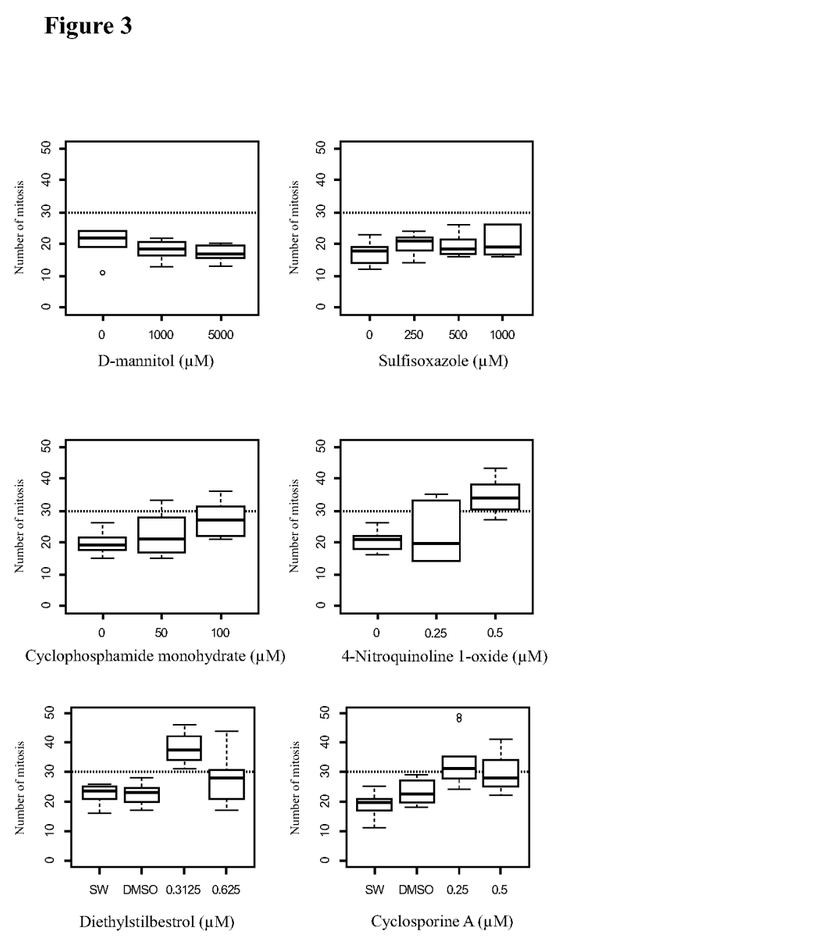
FIG. 3: Box plots representing the mean and IQR of the number of mitotic stem cells in function of the concentration of non-carcinogens D-Mannitol and Sulfisoxazole (Sox); Genotoxic carcinogens 4-Nitroquinoline-1-oxide and Cyclophosphamide monohydrate; and non-genotoxic carcinogens Diethylstilbestrol and Cyclosporine A. Seawater (SW) and DMSO controls are also plotted. All illustrated by one experiment. The dashed line represents the cut-off value of the assay.

D-mannitol was predicted negative by the assay for all three experiments with 0% worms having a number of mitotic stem cells exceeding the cut-off value, even up to 5 mM (910 µg/ml) (FIG. 3 and Table 1). Higher concentrations of Dmann resulted in insolubility in the medium. Sulfisoxazole was predicted negative for all three experiments up to 1 mM. Higher concentrations of Sox resulted in greater than 20% lethality and were not analyzed. In experiment 2, only one Sox concentration (500 µM) resulted in 11.1% of worms exhibiting a number of mitotic stem cells exceeding 30, which is still below our acceptance criteria of 20% (Table 1). In conclusion, both chemicals were finally predicted negative (non-carcinogenic) in the assay (FIG. 3 and Table 1).

Genotoxic Carcinogens

Cyclophosphamide monohydrate was predicted positive in all experiments, each time at 100 µM (26 µg/ml). One experiment with CP was rejected as only three worms were quantified although 66.7% (100 µM) of them had a number of mitotic stem cells exceeding the cut-off value (Table 1).

4-Nitroquinoline-1-oxide resulted in a positive prediction in the assay for two-thirds of the experiments at both 0.25 (0.047 µg/ml) and 0.5 µM (0.095 µg/ml). At the concentrations predicted positive, the percentage of worms exhibiting a number of mitotic stem cells greater than or equal to the cut-off value ranged from 33.3 to 77.8 (Table 1). In the second experiment that was predicted negative, two subsequent concentrations resulted in a percentage of worms exhibiting a number of mitotic stem cells greater than or equal to the cut-off value, but this percentage was, however, not higher than 20% (Table 1). Higher CP and 4NQO concentrations resulted in greater than 20% lethality of the worms and were not analyzed. Altogether, both compounds were finally predicted positive in the assay (FIG. 3 and Table 1).

Non-genotoxic Carcinogens

Diethylstilbestrol was predicted positive for all three experiments at concentrations ranging from 0.3125 µM (0.04 µg/ml) to 0.625 µM (0.1 µg/ml). In experiment one, 0.3125 µM resulted in 100% of worms exhibiting a number of mitotic stem cells exceeding the cut-off value. In two out of three experiments, even two consecutive concentrations within the range were found positive (FIG. 3).

For Cyclosporin A, all experiments fulfilled the acceptance criteria resulting in a positive prediction in the assay. Positive concentrations ranged from 0.125 µM (0.14 µg/ml) to 0.5 µM (0.56 g/ml) with a percentage of mitotic cells greater than or equal to the cut-off value ranging from 36.4% to 70%. Overall, both compounds were predicted positive in the assay (FIG. 3 and Table 1).

TABLE 1

Prediction model. Table representing the number of worms analyzed per concentration (=N), the proportion of worms having 30 or more mitotic stem cells (A), the resulting predictions of all experiments for all tested compounds and the final prediction call.

| Compound (µM) | | Experiment 1 | | | Experiment 2 | | | Experiment 3 | | | Overall prediction |
|---|---|---|---|---|---|---|---|---|---|---|---|
| | | N | %[A] | Pred[B] | N | %[A] | Pred[B] | N | %[A] | Pred[B] | |
| Non-carcinogens | 0 | 6 | 0 | − | 10 | 0 | − | 8 | 0 | − | |
| D-mannitol [C] | 1000 | 8 | 0 | − | 10 | 0 | − | 8 | 0 | − | |
| | 5000 | 8 | 0 | − | 6 | 0 | − | 8 | 0 | − | |
| | | | | Neg | | | Neg | | | Neg | Neg |

TABLE 1-continued

Prediction model. Table representing the number of worms analyzed per concentration (=N), the proportion of worms having 30 or more mitotic stem cells (A), the resulting predictions of all experiments for all tested compounds and the final prediction call.

| Compound (µM) | | Experiment 1 | | | Experiment 2 | | | Experiment 3 | | | Overall prediction |
|---|---|---|---|---|---|---|---|---|---|---|---|
| | | N | %$^A$ | Pred$^B$ | N | %$^A$ | Pred$^B$ | N | %$^A$ | Pred$^B$ | |
| Sulfisoxazole $^C$ | 0 | 9 | 0 | − | 6 | 0 | − | 9 | 0 | − | |
| | 250 | 12 | 0 | − | NA | NA | NA | 9 | 0 | − | |
| | 500 | 9 | 0 | − | 9 | 11.1 | − | 8 | 0 | − | |
| | 1000 | 7 | 0 | − | 10 | 0 | − | 9 | 0 | − | |
| | | | | Neg | | | Neg | | | Neg | Neg |
| Genotoxic carcinogen | 0 | 9 | 0 | − | 6 | 0 | − | 6 | 0 | − | |
| 4-Nitroquinoline-1-oxide $^C$ | 0.125 | NA | NA | NA | 6 | 16.7 | − | NA | NA | NA | |
| | 0.25 | 6 | 33.3 | + | 8 | 12.5 | − | 8 | 37.5 | + | |
| | 0.5 | 9 | 77.8 | + | 7 | 0 | − | 11 | 36.4 | + | |
| | | | | Pos | | | Neg | | | Pos | Pos |
| Cyclophosphamide | 0 | 8 | 0 | − | 9 | 0 | − | 11 | 0 | − | |
| monohydrate $^C$ | 50 | 6 | 0 | − | 8 | 0 | − | 12 | 16.7 | − | |
| | 100 | 3 $^D$ | 66.7 | NA | 10 | 20 | + | 6 | 33.3 | + | |
| | | | | NA | | | Pos | | | Pos | Pos |
| Non-genotoxic carcinogen | 0 | 10 | 0 | − | NA | NA | NA | 8 | 0 | − | |
| Diethylbestrol $^E$ | DMSO | 8 | 0 | − | 6 | 0 | − | 8 | 0 | | |
| | 0.3125 | 10 | 100 | + | 8 | 12.5 | − | 12 | 33.3 | + | |
| | 0.625 | 11 | 27.3 | + | 10 | 50 | + | 9 | 22.2 | + | |
| | | | | Pos | | | Pos | | | Pos | Pos |
| Cyclosporine A $^E$ | 0 | 12 | 0 | − | 8 | 0 | − | 9 | 0 | − | |
| | DMSO | 12 | 0 | − | 6 | 0 | − | 6 | 0 | − | |
| | 0.125 | NA | NA | NA | 7 | 0 | − | 8 | 37.5 | + | |
| | 0.25 | 10 | 70 | + | 7 | 0 | − | 7 | 42.9 | + | |
| | 0.5 | 10 | 40 | + | 11 | 36.4 | + | 8 | 50 | + | |
| | | | | Pos | | | Pos | | | Pos | Pos |

When 20% of the number of mitotic cells in an experiment exceeded the cut-off value of 30, a "+" was scored for that experiment. One "+" per experiment was required for predicting the compound as positive (=Pos) and a minimum of two out of three experiments with positive predictions resulted in a final positive prediction call for that compound (see evaluation criteria in Material and Methods). Concentrations that were not analyzed because of experimental loss during test procedure or rejected because of test invalidity (for example, N < 3 for CP) were coded as not applicable (NA). Dmann: D-Mannitol; Sox: Sulfisoxazole; Nqo: 4-nitroquinoline-1-oxide; Cp: cyclophosphamide monohydrate; Des: diethylstillbestrol; CA: cyclosporine A.
$^A$proportion of worms having 30 or more mitotic stem cells
$^B$+ in case 20% or more worms having 30 or more mitotic stem cells
$^C$ in Seawater (SW)
$^D$ Less than five worms were quantified for this concentration, this experiment was excluded.
$^E$ DMSO conc 0.05%

Test Organism

Asexual strains of the freshwater planarian *Schmidtea mediterranea* (38, 45) were maintained in culture medium, consisting of water, that was first deionized and then distilled, and to which the following nutrients were added: 1.6 mM NaCl, 1.0 mM CaCl2, 1.0 mM MgSO4, 0.1 mM MgCl2, 0.1 mM KCl and 1.2 mM NaHCO3. The animals were continuously kept in the dark at a room temperature of 20° C. and were fed once a week with veal liver.

Experimental Design

Experiments were performed with regenerating animals (heads and tails) to accelerate initial responses to carcinogenic compounds, as this process of massive cell proliferation, migration and differentiation resembles the process of carcinogenesis, and, possibly differently affects the dynamics of stem cells toward genotoxic and non-genotoxic carcinogen exposures (16, 32, 39).

In each experimental condition, animals were cut transversally immediately before exposure to a genotoxic, non-genotoxic or non-carcinogen concentration, medium (control) or medium with DMSO (vehicle control). Exposures were performed in six-well plates (4 ml/well). To exclude intrinsic effects of DMSO on cell proliferation, the DMSO vehicle concentration never exceeded 0.05% and interaction effects between the test compound and DMSO were investigated using a two-way ANOVA (32). Compound selection was based on literature screens (13, 26-28) and included the genotoxic carcinogens methyl methane sulphonate (MMS; Cas # 66-27-3; purity 99%) and 4-nitroquinoline-1-oxide (4NQO; Cas # 56-57-5; purity 98%), the non-genotoxic carcinogens methapyrilene hydrochloride (MPH; 135-23-9; analytical standard), cyclosporine A (CsA; Cas # 59865-13-3; purity ≥98.5%), chlorpromazine hydrochloride (CPZ; Cas # 69-09-0; purity ≥98%) and sodium phenobarbital (S-PB; Cas # 57-30-7) and the non-carcinogen D-mannitol (Dmann, Cas # 69-65-8), all purchased from Sigma-Aldrich (Saint Louis, Mo., USA). After comparing continuous versus intermittent (repeat-dose toxicity: two days of compound exposure, three days of recovery in culture medium) exposures and medium refreshment once versus twice a week, a continuous exposure with medium refreshment twice a week was found most suitable to obtain distinctive cellular responses. Animals were fed once a week with veal liver and starved for one week before stem cell proliferation measurements. Stem cell proliferation was measured after one day of regeneration (the mitotic minimum of regeneration), after three days (the mitotic maximum of regeneration), after one week (the end stage of regeneration) after two and six weeks (during homeostasis), as well as at the appearance of organismal phenotypes (15, 46, 47). Phenotypic effects were monitored daily with a stereo microscope.

Mitotic Activity of Stem Cells

Stem cells are the only proliferating cells in these animals (48). Observed changes in cell proliferation can thus be directly linked to stem cell responses. The mitotic activity of stem cells was determined by immunostaining with anti-P-

Histone H3 antibody (Millipore), performed as previously described (32, 49). After exposure, the worms were treated for 5 minutes on ice with five-eighths Holtfreter (50) solution containing 2% HCI (VWR) to remove the mucus layer. The samples were fixed in Carnoy's fixative (51) for 2 hours (on ice) and were rinsed in 100% methanol (VWR) during 1 hour and bleached overnight at room temperature in 6% $H_2O_2$ (VWR) (in 100% methanol). Subsequently, the worms were rehydrated through a graded series of methanol/phosphate buffered saline-triton (PBST) (PBS tablets; VWR) (TRITON® X-100 pro analyse, VWR) washes (75%, 50%, 25%, 0%) for 10 minutes each, where after non-specific binding sites were blocked in bovine serum albumin (Sigma Aldrich) (PBST/BSA) (0.1% TRITON® X-100, and 0.1 g/ml BSA) for 3 hours. Animals were incubated at 4° C. for 44 hours with a primary antibody (anti-phospho-Histone H3 (Ser10), biotin conjugate, Millipore, catalogue number: 16-189) 1:600 diluted in PBST/BSA. The animals were rinsed repeatedly for 1 hour in PBST and incubated in PBST/BSA for 7 hours. Then, the animals were incubated with a secondary antibody (goat anti-rabbit IgG rhodamine conjugated, Millipore, catalogue number: 12-510), 1:500 diluted in PBST/BSA for 16 hours. Afterwards, animals were rinsed repeatedly for 30 minutes in PBST and mounted in glycerol. The animals were examined with fluorescence microscopy performed with a Nikon Eclipse 80i. The total number of mitotic neoblasts was normalized to the body size of the animals (cfr. Body area). Before the start of the coloring, three photos were taken of each animal at the moment the body was fully stretched. For normalization, of these three photos, the average body size was calculated, using Image J (1.44p, National Institutes of Health).

Phenotypic Follow-up

An in vivo study allows the investigation of the entire organism's response to carcinogenic compounds and, as such, makes it possible to link carcinogen-induced stem cell proliferation with the organism's phenotype. Conditions were subdivided according to their phenotypic effects into concentrations that caused no observable phenotypic effects (category 1), phenotypic effects (category 2, described in phenotypic effect screening) and concentrations that induced organismal death (category 3). Phenotypic parameters that were monitored daily were tissue regression, lesion, blisters, bloating, pigmentation, behavior, regenerative success, body size, tissue outgrowth, flattened posture and organismal death (35). Stem cell proliferation was quantified at the appearance of systemic effects (category 2 concentrations).

Statistical Methods

Figure 4:
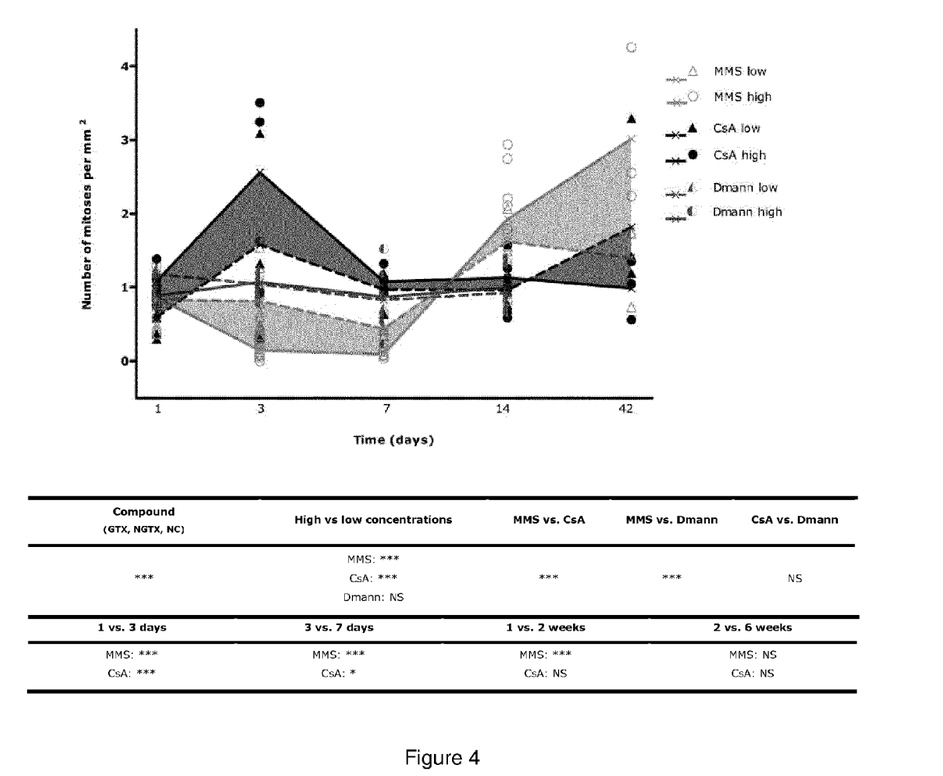
Figure 5:
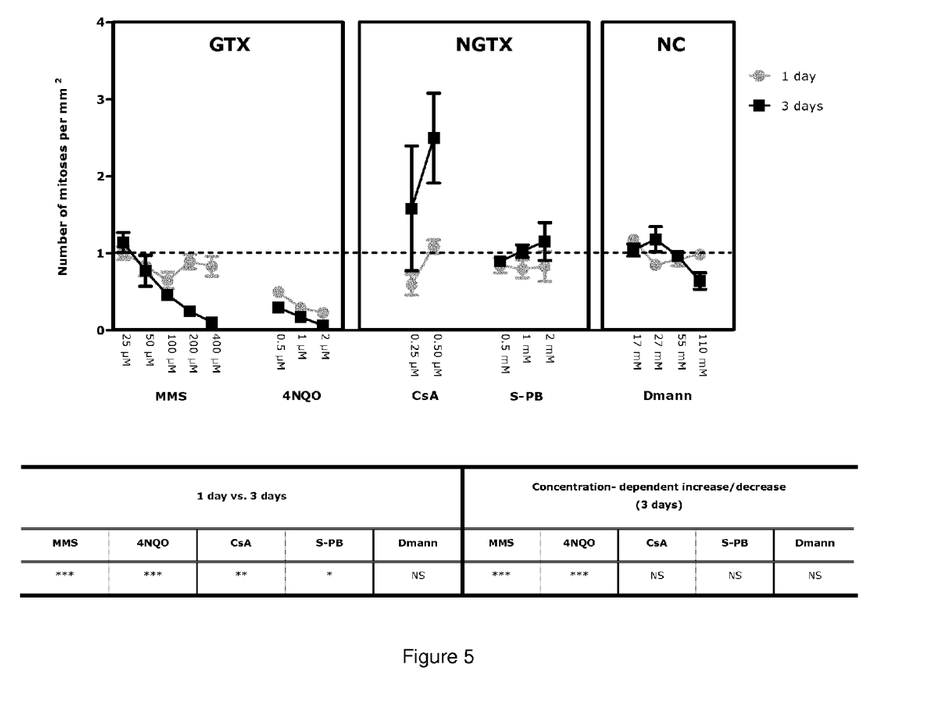
FIG. 5: Comparison of stem cell proliferation responses after one and three days of exposure. Mitotic divisions per $mm^2$ after one and three days of exposure to genotoxic carcinogens (MMS, 4NQO), non-genotoxic carcinogens (CsA, S-PB) and non-carcinogens (Dmann). The number of mitotic cells was normalized against the total body area of the worms and expressed relative to the corresponding MMS, 4NQO, CsA, S-PB and Dmann control group per time point, which was culture medium for all compounds except for CsA, which were exposed to culture medium with 0.05% DMSO (vehicle control). Cell proliferation values of each concentration are connected by lines and are the average and se of minimum three biological repeats. Significant effects are indicated in the table: *$p<0.1$; $p<0.05$; *$p<0.01$. The average and se of MMS control groups are: 172.0±21.9 cells/$mm^2$ (1 day); 368.6±37.4 cells/$mm^2$ (3 days). The average and se of 4NQO control groups are: 293.5±21.6 cells/$mm^2$ (1 day); 452.7±30.3 cells/$mm^2$ (3 days). The average and se of CsA control groups are: 344.1±42.5 cells/$mm^2$ (1 day); 328.3±46.6 cells/$mm^2$ (3 days). The average and se of S-PB control groups are: 289.6±41.1 cells/$mm^2$ (1 day); 424.5±10.9 cells/$mm^2$ (3 days). The average and se of Dmann control groups are.
Figure 6:
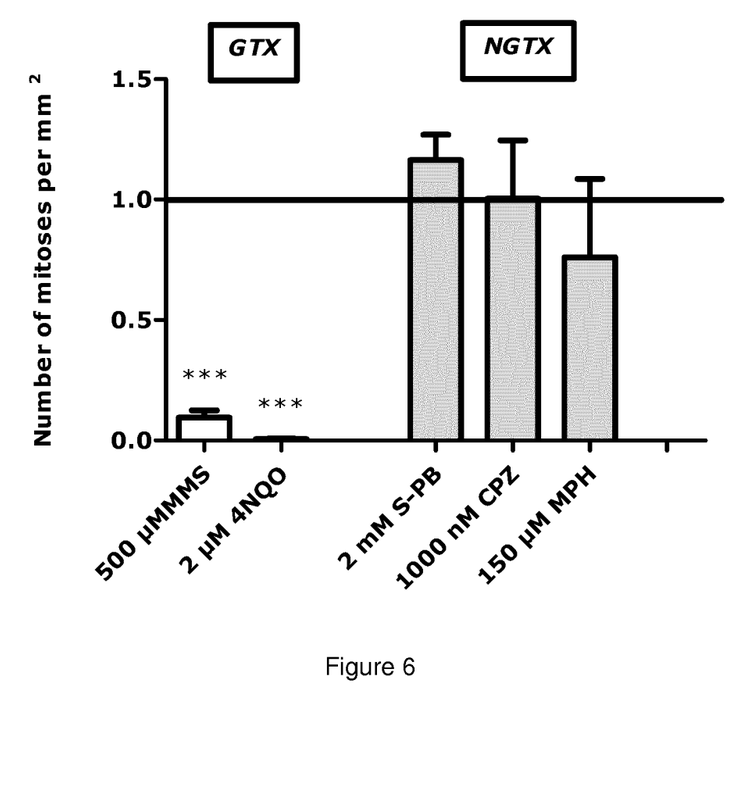
FIG. 6: Stem cell activity responses at the appearance of phenotypic effects. Stem cell proliferation responses at the appearance of phenotypic effects (category 2 concentrations) following genotoxic (MMS, 4NQO) and non-genotoxic (S-PB, CPZ, MPH) carcinogen exposures. The number of mitotic cells was normalized against the total body area of the worms and expressed relative to the corresponding non-exposed group. The values indicated in the graphs are the average±se of minimum three biological repeats, except for S-PB and CPZ, because of severe lysis of the animals. Significant effects as compared to the corresponding control group are indicated with stars: \*\*\*: p<0.01; \*\*: p<0.05. Exposure times were three days (MMS), one week (4NQO) and two weeks (S-PB, CPZ, MPH). The average and se of groups exposed to culture medium are: 227.7±26.7 cells/mm$^2$ (3 days); 212.0±4.7 cells/mm$^2$ (1 week); 130.9±10.2 cells/mm$^2$ (2 weeks). MMS=methyl methane sulphonate; 4NQO=4-nitroquinoline-1-oxide; S-PB=sodium phenobarbital; CPZ=chlorpromazine hydrochloride; and MPH=methapyrilene hydrochloride.

Effects of time and carcinogenic exposures (including low and high concentrations of carcinogens) on the number of dividing cells were analyzed using an ANOVA model including time, exposure and the interaction between both covariates (FIGS. 4 and 5). Effects of carcinogenic exposures on the number of dividing cells were statistically analyzed using an ANOVA model including exposure (FIG. 6). Residuals from the ANOVA model were inspected visually to ensure that the assumptions of constancy of variance and normality of errors were met. If the assumptions of normality were not met, a transformation of the data set was applied (Log, Square root, 1/x and ex). All statistical analyses were performed by using SAS version 9.2 (SAS institute, Cary, N.C., USA). A p-value of less than 0.05 was considered significant. Significance levels of 0.1 level were also reported to empower observed patterns. A general exposure effects is present whenever an exposure to carcinogens has a significantly different effect on the measured parameter in comparison with an exposure to culture medium.

Results

Stem cell proliferation was monitored at physiological meaningful time points after exposure to both low and high concentrations of genotoxic, non-genotoxic and non-carcinogens (FIG. 4). In general, cell proliferation responses following MMS and CsA exposures were significantly distinguishable from each other (p<0.01). The largest differences between genotoxic and non-genotoxic carcinogens were detected before the full achievement of homeostasis (up until two weeks exposure), with notable changes in proliferative responses between one and three days, i.e., a significant decrease for genotoxic carcinogens (p<0.01) compared to a significant increase for non-genotoxic carcinogens (p<0.01). An addition of the non-carcinogen Dmann into the statistical analysis revealed significant differences on cell proliferation responses throughout time between Dmann and MMS exposures (p<0.01), but not with CsA exposures. The concentration (high versus low) of carcinogenic compounds significantly affected mitosis (p<0.01), while the non-carcinogen Dmann had no significant effects on proliferative responses at the different exposure times and concentrations measured.

To assess if the observed differences in cell proliferation after one and three days of exposure are not compound-specific responses, and as such can be generalized to genotoxic and non-genotoxic carcinogens, the organisms were exposed to another genotoxic (4NQO) and non-genotoxic (S-PB) carcinogen (FIG. 5). By focusing on one and three days of exposure, increasing the differential power between genotoxic, non-genotoxic and non-carcinogen-induced stem cell proliferation was attempted. Proliferation significantly differed between one and three days of exposure for the genotoxic carcinogens MMS (p<0.01) and 4NQO (p<0.01) and for the non-genotoxic carcinogens CsA (p<0.05) and S-PB (p<0.1). No significant differences were observed between one and three days of Dmann exposures. A striking result in function of the assay was a stronger inhibition of cell proliferation after three days exposure to genotoxic carcinogens in contrast to a stronger induction of cell proliferation after three days exposure to non-genotoxic carcinogens, both in comparison to proliferative responses after one day exposure. Another valuable result was the significant decrease in cell proliferation for increasing concentrations of genotoxic carcinogens after three days exposure (p<0.01) compared to no significant increases or decreases in cell proliferation for increasing concentrations of non-genotoxic carcinogens.

Phenotypic Effects and Associated Stem Cell Responses.

To further distinguish between carcinogen and non-carcinogen exposures and between genotoxic and non-genotoxic carcinogens, phenotypic effects as a discriminative factor were studied. Exposure concentrations were subdivided into categories, in which category 1 consisted of concentrations that induced no phenotypic effects, category 2 consisted of concentrations that induced phenotypic effects and category 3 were lethal concentrations (Table 2).

TABLE 2

Classification of genotoxic and non-genotoxic carcinogen concentrations according to observed phenotypes.

| Carcinogens | | Toxicity | | |
|---|---|---|---|---|
| | | Cat. 1 | Cat. 2 | Cat. 3 |
| Genotoxic | MMS | 25-50-100-200 µM | 400-500 µM | 1 mM |
| | 4NQO | 0.1-0.5 µM | 2 µM | 5 µM |
| Non-genotoxic | S-PB | 1 mM | 2 mM | 4 mM |
| | CPZ | 250-500 nM | 750-1000 nM | 2 µM |
| | MPH | 10 µM | 150-250 µM | 500 µM |

Concentrations of genotoxic (MMS, 4NQO) and non-genotoxic (S-PB, CPZ, MPH) carcinogens were classified into three categories according to the phenotypic effects they induced: Category 1: No effects on phenotype; Category 2: Phenotypic effects; Category 3: Mortality. For category 2 concentrations in bold, stem cell proliferation responses are presented in the article. Exposure times were three days (MMS), one week (4NQO) and two weeks (S-PB, CPZ, MPH).
MMS: methyl methane sulphonate;
4NQO: 4-nitroquinoline-1-oxide;
S-PB: sodium phenobarbital;
CPZ: chlorpromazine hydrochloride;
MPH: methapyrilene hydrochloride In contrast to carcinogen exposures, no phenotypic effects were induced by non-carcinogen (Dmann) exposures. Category 2 concentrations of genotoxic carcinogens induced phenotypic effects such as aberrant pigmentation spots, severe tissue regression, regeneration failures and aberrant behavior (Table 3).

TABLE 3

Number of animals with specific phenotypic effects after exposure to category 2 concentrations of genotoxic and non-genotoxic carcinogens (see Table 2).

| Phenotypes | GTX | | NGTX | | |
|---|---|---|---|---|---|
| | MMS | 4NQO | S-PB | CPZ | MPH |
| Tissue regression | 3/14 | 2/4 | / | / | / |
| Pigmentation | 1/14 | 2/4 | / | / | / |
| Behavior | 14/14 | 3/4 | 2/2 | 4/4 | 8/8 |
| Regenerative success | 14/14 | 4/4 | / | / | / |
| Body size | 10/14 | / | / | 2/2 | 8/8 |

An exposure to category 2 concentrations of non-genotoxic carcinogens elicited physiological responses, which initially seemed to have a smaller impact on the organism's viability in comparison with genotoxic carcinogen-induced phenotypes, e.g., changes in body size or length or an aberrant behavior. Interestingly, a quantification of cell proliferation at the appearance of phenotypic effects further discriminated genotoxic and non-genotoxic carcinogen exposures: Genotoxic carcinogen-induced phenotypic effects (category 2 concentrations) were associated with a significant drop in stem cell proliferation compared to non-exposed animals, while no proliferation changes were observed at the manifestation of non-genotoxic carcinogen-induced phenotypes (FIG. 6).

REFERENCES

1. EU (2008) 440/2008 of 31 May 2008 laying down test methods pursuant to Regulation (EC) 1907/2006 of the European Parliament and of the Council on the Registration, Evaluation, Authorization and Restriction of Chemicals (REACH), ed (EC) CR (Official Journal of the European Union, L 142/1-L 142/739).
2. Marone P. A., Hall W. C., and Hayes A. W. (2014). Reassessing the two-year rodent carcinogenicity bioassay: a review of the applicability to human risk and current perspectives. *Regulatory toxicology and pharmacology: RTP* 68(1):108-118.
3. Heinonen T., Louekari K., and Tähti H. (2014). Need for Harmonized Strategies and Improved Assessment of Carcinogenic and Genotoxic Potencies of Chemical Substances. *Journal of Translational Toxicology* 1(1):76-87.
4. ICCVAM (2000) ICCVAM Authorization Act of 2000 Public Law 106-545.
5. Doktorova T. Y., Pauwels M., Vinken M., Vanhaecke T., and Rogiers V. (2012). Opportunities for an alternative integrating testing strategy for carcinogen hazard assessment? *Critical Reviews in Toxicology* 42(2):91-106.
6. Ellinger-Ziegelbauer H., Stuart B., Wahle B., Bomann W., and Ahr H. J. (2005). Comparison of the expression profiles induced by genotoxic and nongenotoxic carcinogens in rat liver. *Mutat. Res.* 575(1-2):61-84.
7. Hernández L. G., van Steeg H., Luijten M., and van Benthem J. (2009). Mechanisms of non-genotoxic carcinogens and importance of a weight of evidence approach. *Mutation Research/Reviews in Mutation Research* 682(2-3):94-109.
8. Silva Lima B. and Van der Laan J. W. (2000). Mechanisms of Nongenotoxic Carcinogenesis and Assessment of the Human Hazard. *Regulatory Toxicology and Pharmacology* 32(2):135-143.
9. Bogdanffy M. S. and Valentine R. (2003). Differentiating between local cytotoxicity, mitogenesis, and genotoxicity in carcinogen risk assessments: the case of vinyl acetate. *Toxicology Letters* 140-141(0):83-98.
10. van Delft J. H., et al. (2004). Discrimination of genotoxic from non-genotoxic carcinogens by gene expression profiling. *Carcinogenesis* 25(7):1265-1276.
11. Adler S., et al. (2011). Alternative (non-animal) methods for cosmetics testing: current status and future prospects-2010. *Arch. Toxicol.* 85 (5):367-485.
12. Benigni R., Bossa C., and Tcheremenskaia O. (2013). In vitro cell transformation assays for an integrated, alternative assessment of carcinogenicity: a data-based analysis. *Mutagenesis* 28(1):107-11 6.
13. Kirkland D., Aardema M., Henderson L., and Müller L. (2005). Evaluation of the ability of a battery of three in vitro genotoxicity tests to discriminate rodent carcinogens and non-carcinogens: I. Sensitivity, specificity and relative predictivity. *Mutation Research/Genetic Toxicology and Environmental Mutagenesis* 584(1-2):1-256.

14. Robb S. M. C., Ross E., and Alvarado A. S. (2008). SmedGD: the *Schmidtea mediterranea* genome database. *Nucleic Acids Research* 36 (suppl 1):D599-D606.
15. Dunkel J., Talbot J., and Schotz E. M. (2011). Memory and obesity affect the population dynamics of asexual freshwater planarians. *Phys. Biol.* 8(2):026003.
16. Alexandrov V., Aiello C., and Rossi L. (1990). Modifying factors in prenatal carcinogenesis (review). *In Vivo* 4(5):327-335.
17. Birnbaum L. S. and Fenton S. E. (2003). Cancer and developmental exposure to endocrine disruptors. *Environmental health perspectives* 111(4):389-394.
18. Oviedo N. J. and Beane W. S. (2009). Regeneration: The origin of cancer or a possible cure? *Seminars in Cell and Developmental Biology* 20(5):557-564.
19. Hanahan D. and Weinberg Robert A. (2011). Hallmarks of Cancer: The Next Generation. *Cell* 144(5):646-674.
20. Best J. B. and Morita M. (1982). Planarians as a model system for in vitro teratogenesis studies. *Teratogenesis, carcinogenesis, and mutagenesis* 2(3 -4):277-291.
21. Hall F., Morita M., and Best J. B. (1986). Neoplastic transformation in the planarian: I. Cocarcinogenesis and histopathology. *The Journal of experimental zoology* 240 (2):211-227.
22. Schaeffer D. J. (1993). Planarians as a model system for in vivo tumorigenesis studies. *Ecotoxicology and environmental safety* 25(1):1-18.
23. Hall F., Morita M., and Best J. B. (1986). Neoplastic transformation in the planarian: II. Ultrastructure of malignant reticuloma. *The Journal of experimental zoology* 240(2):229-244.
24. Fu Z. and Tindall D. J. (2008). FOXOs, cancer and regulation of apoptosis. *Oncogene* 27(16):2312-2319.
25. Stalmans S., et al. (2014). Flatworm models in pharmacological research: the importance of compound stability testing. *Regulatory toxicology and pharmacology: RTP* 70(1):149-154.
26. OECD OfECaD (2007). Detailed review on cell transformation assays for detection of chemical carcinogens. *OECD Environment, Health and Safety Publications, Series on Testing and Assessment* No. 31.
27. Kirkland D., Kasper P., Muller L., Corvi R., and Speit G. (2008). Recommended lists of genotoxic and non-genotoxic chemicals for assessment of the performance of new or improved genotoxicity tests: A follow-up to an ECVAM workshop. *Mutation Research/Genetic Toxicology and Environmental Mutagenesis* 653(1-2):99-108.
28. Robinson D. E. and Macdonald J. S. (2001). Background and framework for ILSI's collaborative evaluation program on alternative models for carcinogenicity assessment. *Toxicologic pathology* 29 (1 suppl):13-19.
29. Nimeth K. T., et al. (2004). Stem cell dynamics during growth, feeding, and starvation in the basal flatworm *Macrostomum* sp. (Platyhelminthes). *Developmental dynamics* 230(1):91-99.
30. Pagan O. R., Rowlands A. L., and Urban K. R. (2006). Toxicity and behavioral effects of dimethylsulfoxide in planaria. *Neuroscience letters* 407(3):274-278.
31. Yuan Z., Zhao B., and Zhang Y. (2012). Effects of dimethylsulfoxide on behavior and antioxidant enzymes response of planarian *Dugesia japonica*. *Toxicology and industrial health* 28(5):449-457.
32. Stevens A. S., et al. (2014). Toxicity profiles and solvent-toxicant interference in the planarian *Schmidtea mediterranea* after dimethylsulfoxide (DMSO) exposure. *Journal of applied toxicology: JAT*.
33. Team R D C (2013) R: A language and environment for statistical computing. *R Foundation for Statistical Computing,* Vienna, Austria.
34. Newmark P. A., Reddien P. W., Cebria F., and Alvarado A. S. (2003). Ingestion of bacterially expressed double-stranded RNA inhibits gene expression in planarians. *Proceedings of the National Academy of Sciences* 100 (suppl 1):11861-11865.
35. Reddien P. W., Bermange A. L., Murfitt K. J., Jennings J. R., and Sanchez Alvarado A. (2005). Identification of genes needed for regeneration, stem cell function, and tissue homeostasis by systematic gene perturbation in planaria. *Developmental cell* 8(5):635-649.
36. Ladurner P., Rieger R., and Baguna J. (2000). Spatial distribution and differentiation potential of stem cells in hatchlings and adults in the marine platyhelminth *macrostomum*sp.: a bromodeoxyuridine analysis. *Dev. Biol.* 226(2):231-241.
37. Ladurner P., Scharer L., Salvenmoser W., and Rieger R. M. (2005). A new model organism among the lower Bilateria and the use of digital microscopy in taxonomy of meiobenthic Platyhelminthes: *Macrostomum lignano,* n. sp. (Rhabditophora, Macrostomorpha) Ein neuer Modellorganismus für die basalen Bilaterier und die Verwendung von digitaler Mikroskopie für die Taxonomie meiobenthischer Platyhhelminthen: *Macrostomum lignano* n. sp. (Rhabditophora, Macrostomorpha). *Journal of Zoological Systematics and Evolutionary Research* 43(2): 114-126.
38. Benazzi M., Baguna J., Ballester R., Puccinelli I., and Papa R. D. (1975). Further Contribution to the Taxonomy of the «*Dugesia Lugubris-Polychroa* Group » with Description of *Dugesia Mediterranea* N. SP. (Tricladida, Paludicola). *Bolletino di zoologia* 42(1):81-89.
39. Newmark P. A. and Sanchez Alvarado A. (2000). Bromodeoxyuridine specifically labels the regenerative stem cells of planarians. *Dev. Biol.* 220(2):142-153.
40. Guillard R. R. L. and Ryther J. H. (1962). STUDIES OF MARINE PLANKTONIC DIATOMS: I. CYCLOTELLA NANA HUSTEDT, AND DETONULA CONFERVACEA (CLEVE) GRAN. *Canadian Journal of Microbiology* 8(2):229-239.
41. Rieger R., et al. (1988). Laboratory cultures of marine Macrostomida (Turbellaria). *Fortschr. Zool.* 36:523.
42. Ladurner P., et al. (2008). The stem cell system of the basal flatworm *Macrostomum lignano*. Stem cells (Springer), pp 75-94.
43. Mouton S., et al. (2009). The free-living flatworm *Macrostomum lignano:* a new model organism for ageing research. *Experimental gerontology* 44(4):243-249.
44. Abramoff M. D., Magalhaes P. J., and Ram S. J. (2004). Image processing with ImageJ. *Biophotonics international* 11(7):36-43.
45. Baguna J. (1973). *Estudios citotaxonomicos, ecologicos e histofisiologfa de la regulation morfogenetica durante el crecimiento y la regeneration en la raza asexuada de la planaria Dugesia mediterranea n. sp. (Turbellaria: Tricladida: Paludicola)*.
46. Robb S. M., Ross E., and Sanchez Alvarado A. (2008). SmedGD: the *Schmidtea mediterranea* genome database. *Nucleic acids research* 36(Database issue):D599-606.
47. Salo E. and Baguna J. (1984). Regeneration and pattern formation in planarians. I. The pattern of mitosis in anterior and posterior regeneration in *Dugesia* (G) *tigrina,* and a new proposal for blastema formation. *Journal of embryology and experimental morphology* 83:63-80.

48. Reddien P. W. and Alvarado A. S. (2004). Fundamentals of planarian regeneration. *Annual review of cell and developmental biology* 20:725-757.
49. Plusquin M., et al. (2012). Physiological and molecular characterisation of cadmium stress in *Schmidtea mediterranea*. *The International journal of developmental biology* 56(1-3):183-191.
50. Armstrong J. B., Duhon S. T., and Malacinski G. M. (1989). Raising the axolotl in captivity. *Smith VII*.
51. Yoneyama M., Kitayama T., Taniura H., and Yoneda Y. (2003). Immersion fixation with Carnoy solution for conventional immunohistochemical detection of particular N-methyl-D-aspartate receptor subunits in murine hippocampus. *Journal of neuroscience research* 73(3):41 6-426.
52. Doktorova T Y, et al. (2014). Testing chemical carcinogenicity by using a transcriptomics HepaRG-based model?
53. Hochstenbach K, et al. (2012). Transcriptomic fingerprints in human peripheral blood mononuclear cells indicative of genotoxic and non-genotoxic carcinogenic exposure. *Mutation Research/Genetic Toxicology and Environmental Mutagenesis* 746(2):124-134.

The invention claimed is:

1. A method for determining whether a compound is a genotoxic carcinogen, the method comprising:
cutting a flatworm transversally in order to create at least one regenerating flatworm,
exposing a regenerating flatworm therefrom to the compound for a period of time and at a concentration that triggers phenotypic effects in regenerating flatworms,
determining the number of adult pluripotent stem cells, excluding gonadal phosphorylated H3-positive cells, within said regenerating flatworm after exposure to the compound, wherein the number of adult pluripotent stem cells, excluding gonadal phosphorylated H3-positive cells is determined with a phosphorylated histone H3 immunoassay, and
comparing the number of adult pluripotent stem cells, excluding gonadal phosphorylated H3-positive cells, within the regenerating flatworm after exposure to the compound to the number of adult pluripotent stem cells, excluding gonadal phosphorylated H3-positive cells, within a regenerating flatworm obtained by a similar exposure to a non-carcinogenic, control compound,
so as to classify the compound as a genotoxic carcinogen when the determined number of adult pluripotent stem cells, excluding gonadal phosphorylated H3-positive cells, is significantly lower than the number of adult pluripotent stem cells, excluding gonadal phosphorylated H3-positive cells, within a regenerating flatworm after the similar exposure to the non-carcinogenic, control compound.

2. The method according to claim 1, wherein the period of time that triggers phenotypic effects in regenerating flatworms is between 3 and 19 days.

3. The method according to claim 1, wherein said phenotypic effects are selected from the group consisting of aberrant pigmentation spots, tissue regression, lesions, blisters, bloating, behavioral changes, difficulties in regeneration, abnormal body size, tissue outgrowth and flattened posture.

4. A method of detecting whether a compound is a non-genotoxic carcinogen, the method comprising:
cutting a flatworm transversally in order to create at least one regenerating flatworm,
exposing the regenerating flatworm to the compound for at least three (3) days,
determining the number of adult pluripotent stem cells, execluding gonadal phosphorylated H3-positive cells, within said regenerating flatworm after said exposure to the compound, wherein the number of adult pluripotent stem cells, excluding gonadal phosphorylated H3-positive cells, is determined with a phosphorylated histone H3 immunoassay, and
comparing the number of adult pluripotent stem cells, excluding gonadal phosphorylated H3-positive cells, within the regenerating flatworm after exposure to the number of adult pluripotent stem cells, excluding gonadal phosphorylated H3-positive cells, within a regenerating flatworm obtained by a similar exposure to a non-carcinogenic, control compound, so as to classify the compound,
wherein the compound is classified as a non-genotoxic carcinogenic when there is a concentration-dependent increase in the number of adult pluripotent stem cells, excluding gonadal phosphorylated H3-positive cells, at day 3 post-exposure,
wherein the compound is classified as a genotoxic carcinogenic when there is a concentration-dependent decrease in the number of adult pluripotent stem cells, excluding gonadal phosphorylate H3-positive cells, at day 3 post-exposure, and
wherein the compound is classified as non-carcinogenic when there is no concentration-dependent change in the number of adult pluripotent stem cells, excluding gonadal phosphorylated H3-positive cells, at day 3 post-exposure.

5. The method according to claim 1, wherein the flatworm is *Macrostomum lignano* or *Schmidtea mediterranea*.

6. The method according to claim 4, wherein the flatworm is *Macrostomum lignano* or *Schmidtea editerranea*.

7. A method for determining whether a compound is a genotoxic carcinogen, the method comprising:
cutting a flatworm transversallv in order to create at least one regenerating flatworm,
exposing a first regenerating flatworm to a test compound at a concentration and for a period of time that is at least three (3) days;
determining the number of adult pluripotent stem cells, execluding gonadal phosphorylated H3-positive cells, within the first regenerating flatworm after the period of time, wherein the number of adult pluripotent stem cells, excluding gonadal phosphorylated H3-positive cells, is determined with a phosphorylated histone H3 immunoassay;
exposing a second regenerating flatworm to a non-carcinogenic, control compound for the period of time that the first regenerating flatworm was exposed to the test compound; and
determining the number of adult pluripotent stem cells, excluding gonadal phosphorylated H3-positive cells, within the second regenerating flatworm after treatment with the non-carcinogenic, control compound with a phosphorylated histone H3 immunoassay,
wherein the test compound is determined to be a genotoxic carcinogen when the number of adult pluripotent stem cells, excluding gonadal phosphorylated H3-positive cells, determined in the first regenerating flatworm is significantly less than the number of adult pluripotent stem cells, excluding gonadal phosphorylated H3-positive cells, determined in the second regenerating flatworm.

* * * * *

UNITED STATES PATENT AND TRADEMARK OFFICE
CERTIFICATE OF CORRECTION

PATENT NO. : 10,197,556 B2
APPLICATION NO. : 15/557930
DATED : February 5, 2019
INVENTOR(S) : Karen Smeets et al.

It is certified that error appears in the above-identified patent and that said Letters Patent is hereby corrected as shown below:

In the Claims

| | | | |
|---|---|---|---|
| Claim 4, | Column 22, | Line 4, | change "execluding gonadal" to --excluding gonadal-- |
| Claim 4, | Column 22, | Line 27, | change "gonadal phosphorylate" to --gonadal phosphorylated-- |
| Claim 6, | Column 22, | Line 37, | change "*Schmidtea editerranea.*" to --*Schmidtea mediterranea.*-- |
| Claim 7, | Column 22, | Line 40, | change "flatworm transversallv" to --flatworm transversally-- |
| Claim 7, | Column 22, | Line 46, | change "exeluding gonadal" to --excluding gonadal-- |

Signed and Sealed this
Fifth Day of March, 2019

Andrei Iancu
*Director of the United States Patent and Trademark Office*